United States Patent [19]
Kelly et al.

[11] Patent Number: 4,549,546
[45] Date of Patent: Oct. 29, 1985

[54] BONE GROWTH STIMULATOR

[75] Inventors: P. Richard Kelly, Hales Corner; John N. Pedersen, New Berlin, both of Wis.

[73] Assignee: Telectronics Pty. Ltd., Lane Cove, Australia

[21] Appl. No.: 567,170

[22] Filed: Dec. 30, 1983

[51] Int. Cl.[4] ............................................. A61N 1/20
[52] U.S. Cl. ................................................. 128/419 F
[58] Field of Search .......... 128/419 C, 419 E, 419 F, 128/419 P, 419 PG, 419 PS

[56] References Cited

U.S. PATENT DOCUMENTS

| | | | |
|---|---|---|---|
| 3,683,932 | 8/1972 | Cole | 128/419 P |
| 4,041,956 | 8/1977 | Purdy et al. | 128/419 PS |
| 4,333,469 | 1/1982 | Jeffcoat et al. | 128/419 F |

FOREIGN PATENT DOCUMENTS

| | | | |
|---|---|---|---|
| 480202 | 3/1975 | Australia | 128/419 F |
| 2552523 | 8/1976 | Fed. Rep. of Germany | 128/419 F |

Primary Examiner—William E. Kamm
Attorney, Agent, or Firm—Gottlieb, Rackman & Reisman

[57] ABSTRACT

An implantable electrical bone growth stimulator having a case made of metal, a current source in the case, an anode and at least one cathode lead electrically connected to the current source and exiting the case. The case has a thin, flat-sided shape with a rectangular cross-section. The current source is a circuit board and electrical components that are arranged on the circuit board to form a completed assembly positioned completely within the case, and the anode is an area of the case that is platinum plated.

4 Claims, 7 Drawing Figures

BONE GROWTH STIMULATOR

DESCRIPTION

Background of the Invention

This invention relates to electrical bone growth stimulators. It has been known for over twenty years that bone growth and bone-to-bone fusion can be acceleratd by electrical stimulation. The mechanism by which bone growth is thus accelerated is not completely understood. However, numerous experimenters have verified its existence. Prior art electrical bone growth stimulators have been external, internal, partially invasive, direct current, alternating current, pulsed magnetic, metal encapsulated, and plastic encapsulated.

A bone growth stimulator of the type herein described is a constant-current source. The device typically includes one anode, and one or more cathodes. The anode may be inserted in soft tissue, and the one or more cathode leads are implanted into the bone, using known techniques, in the area of a fracture. The device typically generates a 20-microampere current which stimulates bone growth around the cathode or cathodes. A constant-current source is utilized so that the current does not vary with the impedance between the electrodes.

The human body is generally a hostile environment for electronic devices. An unprotected electronic device will be quickly rendered inoperative by liquid and ionic contaminants. If precautions are not taken to prevent contamination of the electrical components in the device, it may take only days or weeks before the unit ceases to function.

Hermetic-sealing manufacturing processes, applicable to implantable electronic devices such as pacemakers, are complex and costly. If hermetic sealing cannot be cost-justified, it is important that the "next-best thing" be done to avoid contamination. Prior art bone growth stimulators have not generally offered maximum reliability in this regard especially if plastic encapsulated. Also, because of the small size of bone growth stimulators, the compatibility of the manufacturing process thereof with hermetic sealing has been difficult.

Prior art bone growth stimulators have also exhibited "mechanical" problems. While size is not usually a critical factor when it comes to certain electromedical implantable prosthetic devices such as pacemakers, that is not always the case with bone growth stimulators. There is often not enough room in a human arm or leg to implant a bulky device. This is especially true in small children six months of age and older where electrical stimulation may be used, for example, as a treatment for congenital pseudoarthrosis.

Prior art devices have also failed to exhibit a shape that affords the ease of implantation and removal which is desired. Prior art devices, for the most part, have been of a shape that is uncomfortable for the patient using the device in one or more respects. When cylindrical devices are used, such as those described in U.S. Pat. No. 4,333,469, this discomfort is attributable to the rotation of the device when implanted. This can also lead to abrading of the epidermis over the unit which may cause it to become exposed. This is especially a problem when used where little flesh is available within which to imbed the stimulator.

Another problem with a cylindrical device of the type shown in U.S. Pat. No. 4,333,469 is the indirect connection of electronics to the electrical components comprising the constant-current source. In that device the electrical components are indirectly connected by means of metal ribbons. This indirect connection could result in decreased reliability due to an increased possiblity of breakage during handling. However, this type of unit shape continues to be useful and reliable in many environments.

In prior art devices, epoxy potting compounds were used to encase the constant-current source. Epoxy is strong and a surgeon can grip an epoxy case with forceps during the implant procedure; but epoxy materials are not the best choice for long life because they produce ionic and/or polar by-products when exposed to water vapor. These by-products can short the circuit elements. Silicone elastomers, on the other hand, are chemically much more stable barriers to water vapor but are mechanically weak and can be damaged when gripped by forceps. The device of U.S. Pat. No. 4,333,469 was metal encased, an improvement over the epoxy-potted unit but still susceptible to attack by body fluids if implanted for too long a period. Hermetic sealing, for example as disclosed in Patent U.S. Pat. No. 4,414,979, represented an improvement in that regard. The device of this patent also introduced the ability to monitor battery life.

Still another shortcoming exhibited by some prior art bone growth stimulators is tissue damage which occurs when removing the cathode lead or leads. There is also a problem of lead breakage due, for example, to flexing when implanted. The cathode itself cannot be removed from the bone into which it is implanted; bone grows around it. What is sometimes done is to make a separate incision for the sole purpose of cutting the cathode lead at the bone site. An alternative to making an incision, in addition to that required to remove the bone growth stimulator itself, is to pull on the cathode lead; the lead usually breaks at the desired place where it exits the bone. But what then often happens is that tissues are damaged as the cathode lead is withdrawn from the body. It has been proposed to put a quick-disconnect joint in the cathode lead to facilitate removable and/or replacement of the power source when a unit battery runs down. However, improved resistance to accidental lead breakage continues to be desirable.

OBJECTS OF THE PRESENT INVENTION

It is therefore an object of the present invention to provide a bone growth stimulator with a certain shape that is comfortable for the patient when it is implanted, allows easier implantation and removal, and resists movement in the body when implanted.

It is another object of the present invention to provide a bone growth stimulator that is more reliable than prior art devices.

Other objects and advantages of the present invention will become apparent from the following description.

SUMMARY OF THE INVENTION

According to the present invention an improvement has been discovered in an implantable bone growth stimulator of the type having a case, an anode and at least one cathode lead electrically connected to the current source and exiting the case.

The improvement comprises a case having a thin, flat-sided shape with a rectangular cross-section; the current source is a single circuit board whose electrical components, including the battery, are arranged on the circuit board to form an assembly which is positioned completely within the case; and the anode is an area of the case that is platinum plated.

DESCRIPTION OF THE PREFERRED EMBODIMENT

This invention is a constant current generator powered by a lithium halide battery with electrode lead configurations designed to aid the healing of bones. The electronics and power source are hermetically sealed in a titanium case part of which is coated in platinum and acts as the anode.

Figure 1:
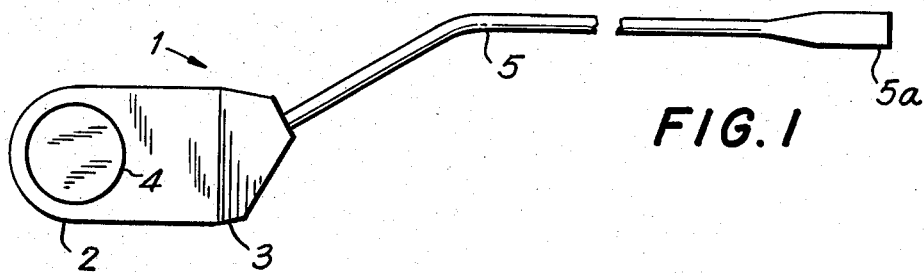
FIG. 1 depicts the bone growth stimulator of the invention.
Figure 1A:
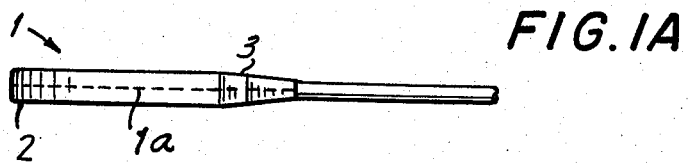
FIG. 1A is a side elevation view of the bone growth stimulator of FIG. 1.

The bone growth stimulator of FIG. 1 consists of three-part, flat-sided metal housing 1, preferably 99% titanium, with a rectangular cross-section. The housing is preferably made by welding two mirror image case halves as better seen in FIG. 1A, the dotted line 1a indicating the weld line; or it can be a deep drawn case. This houses the constant-current source. The housing consists of a main case 2, a metal top cap 23 (not shown in FIG. 1) welded to the main case 2, and a Silastic top 3 bonded by a silicone elastomer potting compound on the top cap 23. The cathode lead 5 exits through a hole at the top of the Silastic top 3. An open topped Teflon boot 2a (shown in dotted lines in FIG. 2 to maintain drawing simplicity) is placed over the electronics within the main case 2 to insulate and protect the electronics. A polymide film 2b is placed over the Teflon as further protection for the circuitry. It consists of a rectangular sheet folded over on itself and taped at 2c (see FIG. 2A) to form a cylinder. Another piece of tape 2d attaches the film cylinder to the Teflon boot.

The thin rectangular shape of the bone growth stimulator of this invention helps prevent abrasion, after implantation, through the skin in areas of little flesh. This shape also prevents rotation of the device when it is implanted so it is more comfortable to the patient. It further reduces undesirable flexing and twisting that may occur with the prior art cylindrical shapes. The rectangular cross-sectional shape is easier to hold and manipulate than a cylindrical or more nearly circular cross-sectional shape making implantation easier. When the top cap 23 is welded on to the main case 2 to hermetically seal the electronics and constant-current source, the rectangular shape and thin case material allow heat to be dissipated in a more efficacious manner. This allows the device to withstand greater heat stress during welding when hermetically sealing. This in turn results in greater reliability because of less chance of mechanical breakage or breakdown of electrical components. Cylindrical prior art devices caused heat to be concentrated in a circular configuration which often led to deformation of the metal closure or main case and contents.

The surface area 4 of the main case 2 is platinum-plated for anodic function. This surface area should be at least about 165 mm$^2$ for the mode herein described.

The cathode lead 5 is preferably constructed of DBS (Drawn-Brazed-Stranded) 316LUM stainless steel with a silver braze material.

The illustrative embodiment of the invention is designed for "long-bone" fusion and it includes a single long cathode lead 5. For spinal fusions, a slightly different unit (not shown) should be used. The lead 5 is shown terminating in the female connector or socket 5a. This connector is designed to receive a lead adapted to be placed in the fracture site. (See copending application Ser. No. 237,090 entitled "Bone Growth Stimulator Connector", filed on Feb. 23, 1981 in the name of John M. Dickson, for more details of this type of lead construction.)

Figure 5:
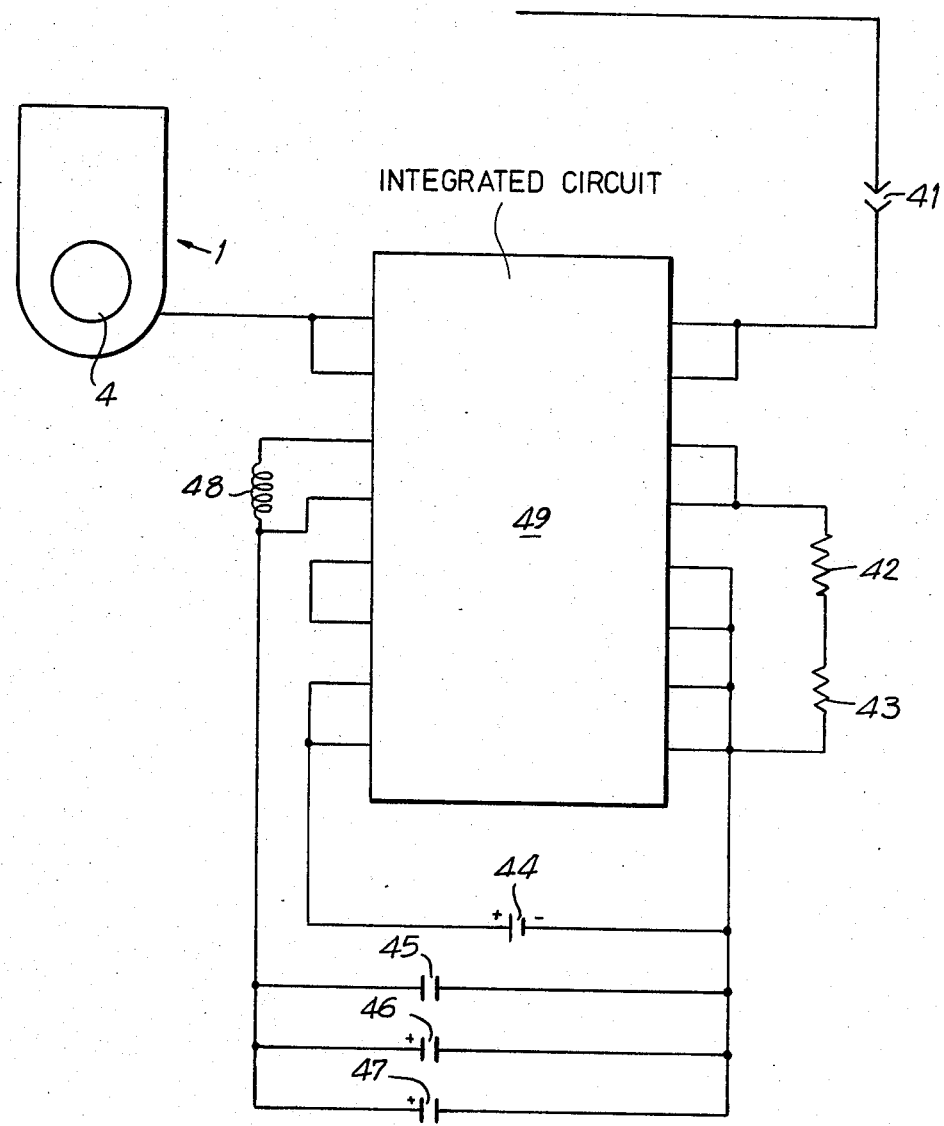
FIG. 5 is a schematic of the electrical circuit.

The constant-current generator shown in FIG. 5 is similar to that disclosed in U.S. Pat. No. 4,414,979; it includes one lithium halide battery 44 for longer life, two resistors 42, 43, three capacitors 45, 46, 47, an inductor 48 and an integrated circuit 49. The battery is directly connected to the board, as shown in FIG. 2.

The electronic circuitry acts as a self-adjusting variable resistance between the energy source and the load impedance (bone/tissue resistance). This assures a constant current will flow regardless of changes in the load between the limits of 0–100 kohms.

Figure 2:
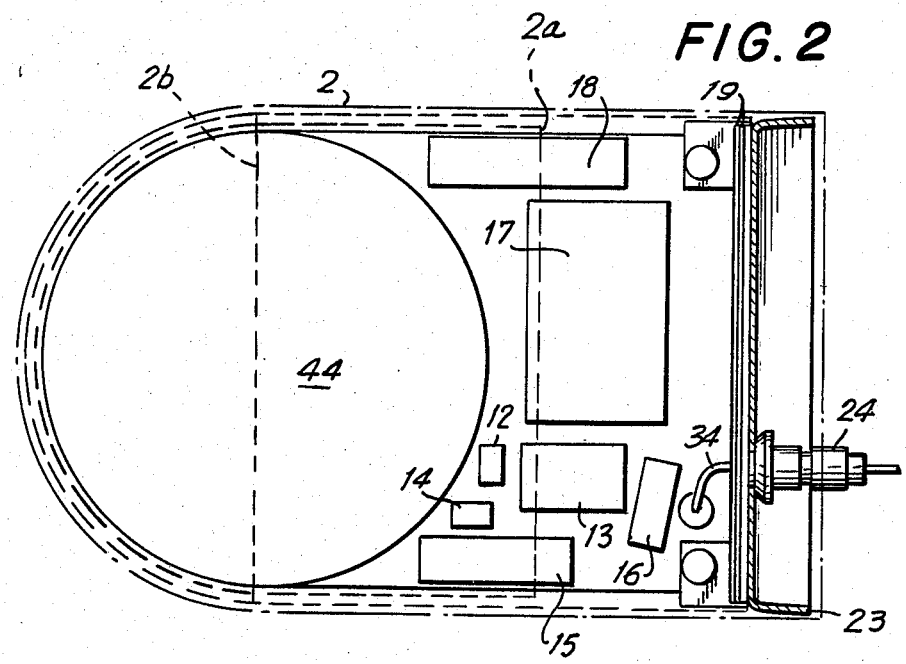
FIG. 2 illustrates the arrangement of the electrical components on the printed circuit board, the top cap and the feed-through assembly.
Figure 2A:
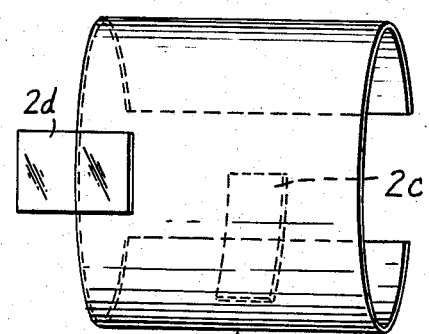
FIG. 2A depicts a polymide sheet used to encase the circuit board.

The physical arrangement of the components on the printed circuit board is depicted in FIG. 2. The components shown are the battery 44, three chip capacitors 12, 13 and 14, two resistors 15 and 16, integrated circuit 17 and the inductor 18.

Also shown in the mica insulation 19 which forms a heat shield which helps to protect the components during welding. Together with the top cap 23 it provides a reinforcing means to maintain integrity of the top while welding is being done. The top cap 23 also serves to conduct heat during welding to the outer case which serves as a heat sink.

Figure 3:
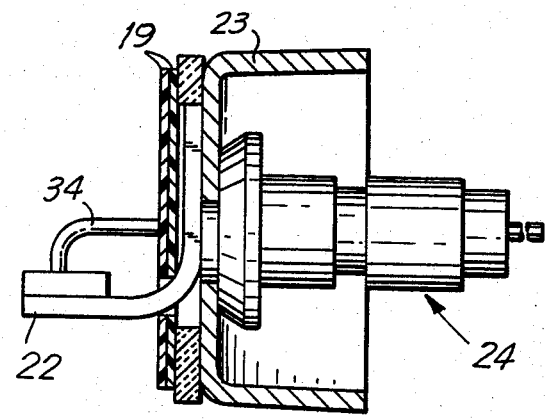
FIG. 3 is a side elevation view of the top cap and feed-through assembly.

Brackets 22 (see FIG. 3) are rigidly fixed to the main case 2. This protects the terminal top from distortion during welding while also providing a positive ground. It also removes undesirable flexibility from the mount which was present in the cylindrical design. There is no tension on the connection of the feed-through assembly 24 to the circuit board because of the physically positive connection to the case. In the prior construction the tendency for parts to move during expansion and contraction under the thermal stresses of welding prevented such a rigid construction scheme, and a small feed-through.

The use of a single flat printed circuit board provides more room to lay out the electrical components in a logical manner. The components are tab-mounted, i.e., they are directly soldered to the circuit board. This direct connection means that there is less chance for breakage. The cylindrical construction required a less satisfactory stacked (cordwood) arrangement.

Figure 4:
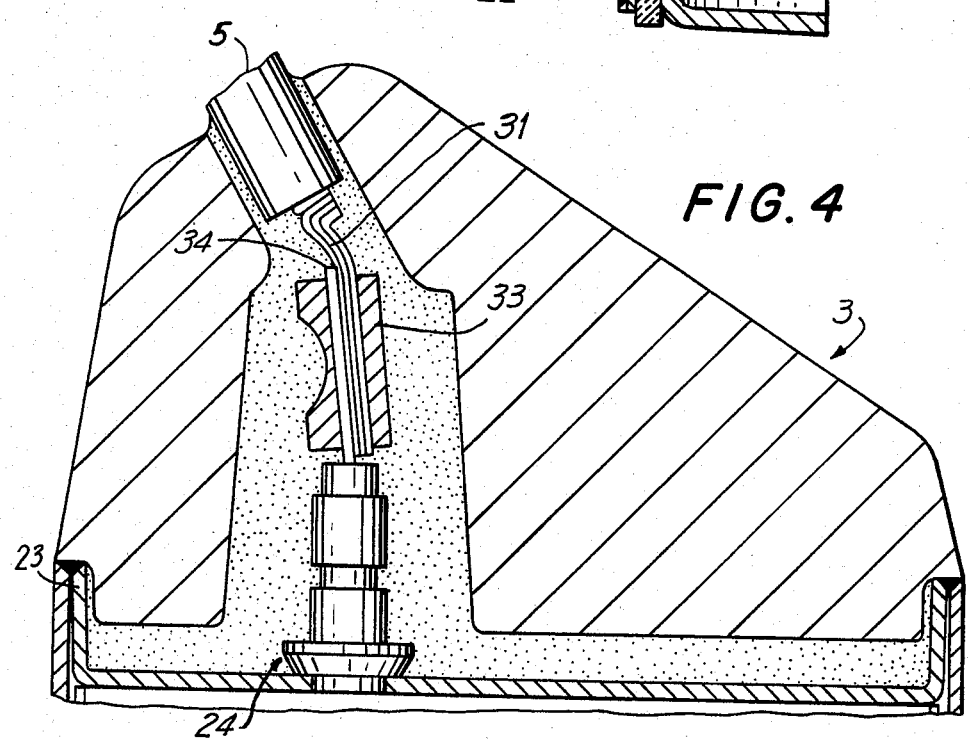
FIG. 4 illustrates the Silastic top positioned over the feed-through assembly and joined to the top cap.

FIG. 4 depicts the Silastic top 3 placed over the feed-through assembly 24 and joined to the top cap 23. A platinum clad titanium wire 34 is soldered to the circuit board and fed through the top cap 23 via the feed-through assembly 24. Upon exiting the feed-through assembly 24 the platinum clad titanium wire 34 is placed in contact with the stainless steel (DBS) wire 31 by means of a connector 33. This feed-through assembly, upon leaving the Silastic top 3, is sheathed in Silastic tubing. This cathode lead 5 terminates where the lead wire 31 is attached to a titanium connector socket 5a.

The top cap 23, when welded to the case 2, hermetically seals the circuitry and battery contained therein. Case welding may be done by GRA (gas tungsten arc), electron beam, or laser among other methods. The feed-through assembly 24 and that portion of the cathode lead 5 within the Silastic top 3 are potted in a conventional manner to prevent ionic contamination and secure the Silastic top 3 in place. The preferred potting material is Dow Corning Silastic medical adhesive, type "A".

Titanium is the best metal to use to form the case. Titanium not only provides mechanical strength but it is probably the best tolerated implant metal. Stainless steel or cobalt-chrome may also be employed, but these are less desirable.

The titanium case by itself cannot function properly as an anode because an oxide forms on it and limits the current to levels below 20 ua. But placing a platinum spot on the titanium case improves its anode capability. Thus, by platinizing an area of the case that is at least 165 mm$^2$ the case will function properly as an anode.

It should also be noted that both ends of the case are rounded and that all edges are beveled.

The device of this invention is the subject of a submission to the U.S. FDA, PMA number P 790005/S16.

In the preferred embodiment of the invention the power source is Model 1935-M cell manufactured by Catalyst Research Corp. The device is gas sterilized. It weighs 8 grams and is 44 mm by 2 mm by 5 mm in outside dimensions. The case is approximately 35.25 mm long. The case wall thickness is approximately 0.4 mm. The radius of curvature of the curved end of the case is approximately 10.90 mm. Other materials of construction and components are the same as described in the patents mentioned above.

Silicone elastomer materials are used for potting the device in a known manner. However, they are not the only potting compounds which can be employed, for example, bee's wax may be used. In general, the potting compound should allow out-gasing, the impervious to liquids, and nonproductive of ionic and polar molecules. Silastic materials are ideal in this regard because they adhere to titanium. The bond which forms insures that there is minimum space between the potting encapsulant and the case where bacteria could have become entrapped. Also, a most likely path for the ingress of water would be along the case wall, and a tight bond prevents this from happening.

We claim:

1. In an implantable bone growth stimulator, said stimulator being encapsulated in a case made of metal which case functions as the stimulator housing, a constant current source in the case, at least one cathode lead electrically connected to the current source, there being an electrical connection between the stimulator housing and the current source, and there being electronics in the case electrically connected to the power source; the improvement comprising:

said case being thin walled, and having a flat-sided shape of substantially rectangular cross-section, said case being defined by a pair of substantially parallel top and bottom walls, there being opposed side walls extending between said top and bottom walls and being substantially narrower than said top and bottom walls, and opposed end walls, a first said end wall being substantially smaller than said side walls;

said first end wall comprising a top cap welded to adjacent edges of the adjacent top, bottom and side wall edges to form a hermetic seal over said electronics and said current source contained within the case;

a feed-through assembly welded to the top cap and interconnected to said at least one cathode lead and the contained current source, the feed-through assembly being longitudinally off center of the top cap;

brace means substantially rigidly interconnected between the top cap and adjacent walls of the case internally of the case which they form, constructed and arranged to provide a positive ground for the unit and protect the top cap from distortion thereof in relation to the adjacent side walls, said brace means further constructed and arranged to counteract expansion and contraction of the adjacent parts;

an elastomer top placed over the feed-through assembly, there being means joining said elastomer top to the top cap; and an electrically-insulating plastic boot and insulator about the current source.

2. The device of claim 1 wherein the current source is a circuit board and electrical components arranged and soldered onto the circuit board.

3. The device of claim 1 wherein the anode is a platinum-plated area of the case.

4. The device of claim 1 wherein the anode is a platinum plated area of the case.

* * * * *